United States Patent [19]

Sherwin et al.

[11] 4,399,295

[45] Aug. 16, 1983

[54] PROCESS FOR PREPARING OXIRANE COMPOUNDS

[75] Inventors: Martin B. Sherwin, London, England; Marshall E. Frank, Chappaqua, N.Y.

[73] Assignee: Chem Systems Inc., New York, N.Y.

[21] Appl. No.: 36,153

[22] Filed: May 4, 1979

Related U.S. Application Data

[63] Continuation-in-part of Ser. No. 919,792, Jun. 28, 1978, abandoned, which is a continuation-in-part of Ser. No. 861,803, Dec. 19, 1977, abandoned.

[51] Int. Cl.$^3$ .................................................. C07D 301/02
[52] U.S. Cl. ........................................................ 549/518
[58] Field of Search .................................... 260/348.16

[56] References Cited

U.S. PATENT DOCUMENTS

Re. 29,597  3/1978  Brownstein et al. ........... 260/348.16
4,012,424  3/1977  Sherwin et al. ................ 260/348.16

*Primary Examiner*—Norma S. Milestone
*Attorney, Agent, or Firm*—Bert J. Lewen

[57] ABSTRACT

A process for preparing oxirane compounds by the deacyloxylation of a vicinal hydroxyester in the presence of a basic material which comprises carrying out the reaction in a dilute phase transport reactor into which is fed a stream of heated catalyst co-current with a feed gas stream. The catalyst is heated in a fluidized bed heater. The catalyst and product gases are separated in a cyclone separator, the catalyst being returned to the heater and the effluent product gas being further processed to recover product.

13 Claims, 1 Drawing Figure

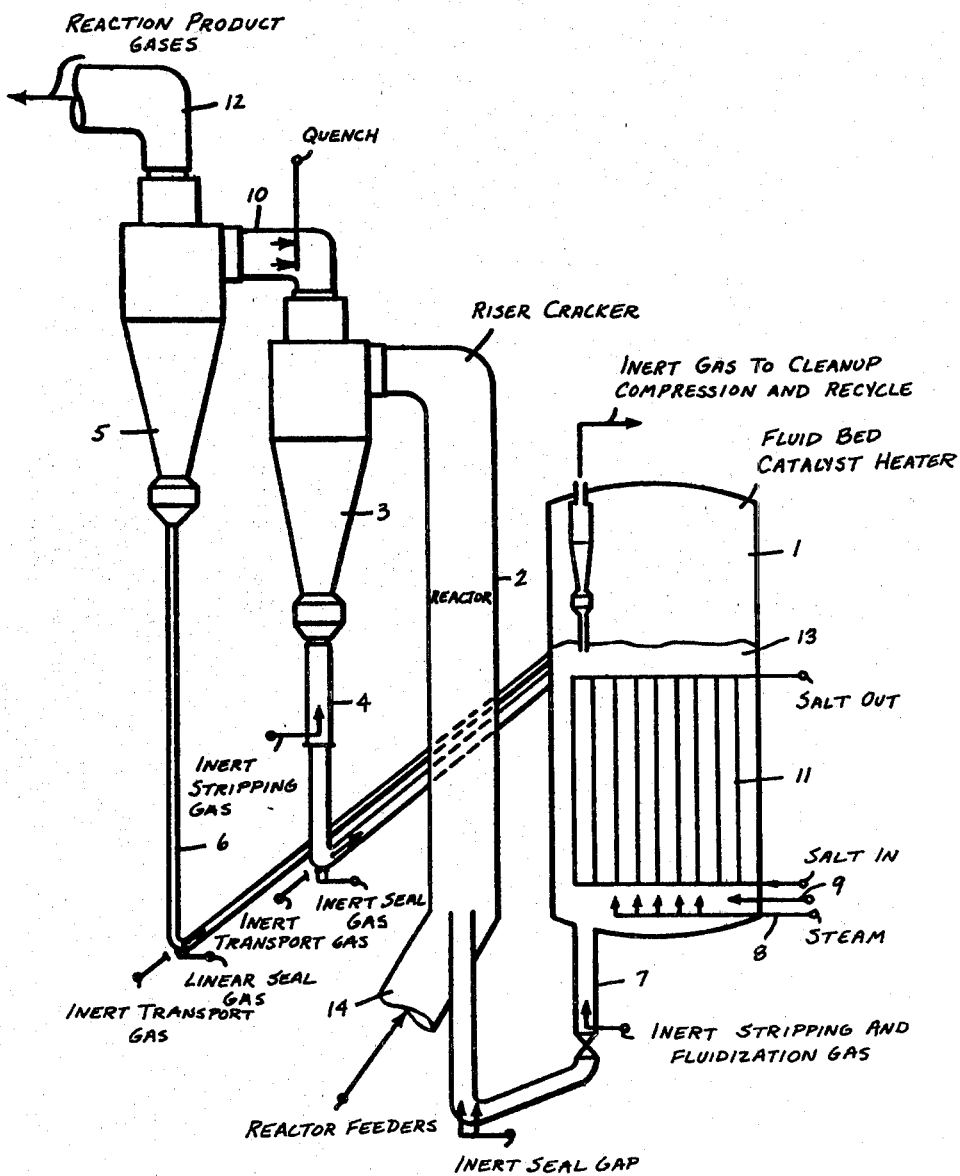

PROCESS FOR PREPARING OXIRANE COMPOUNDS

RELATED APPLICATIONS

This application is a continuation-in-part of U.S. patent application Ser. No. 919,792, filed June 28, 1978, which, in turn, is a continuation-in-part of U.S. patent application Ser. No. 861,803, filed Dec. 19, 1977, both now abandoned.

BACKGROUND OF THE INVENTION

A process for the vapor phase production of oxirane compounds is taught in U.S. Pat. No. Re. 29,597, reissued Mar. 28, 1978, original U.S. Pat. No. 4,012,423, issued on Mar. 15, 1977 incorporated herein by reference. Although that patent gives a complete description of the process, so much of that disclosure as is necessary for clarity will be repeated in this application. The process utilizes as a starting material a vicinal hydroxyester described by the general formula

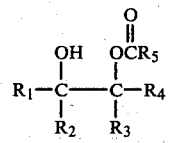

wherein $R_1$, $R_2$, $R_3$, $R_4$, and $R_5$ may be H, alkyl, alkenyl or alkynyl of about 1 to 16 carbon atoms; an aryl, such as phenyl or naphthyl; cyano;

wherein $R_6$ is H, alkyl, alkoxy, carbomethoxy, or carboacyl. Preferably at least two of the aforesaid groups are H and the remaining R groups are H, methyl, ethyl, propyl, butyl or phenyl. The oxirane compound is prepared by the deacyloxylation of the vicinal hydroxyester in the presence of a basic material. The reaction products are oxirane compounds of the general formula

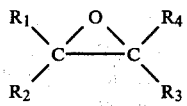

and $R_5COOH$ wherein $R_1$, $R_2$, $R_3$, $R_4$, and $R_5$ are as previously described.

The aforementioned U.S. Pat. No. 4,012,423 teaches methods for preparing the oxirane compounds using a batch process with respect to the basic catalyst material. Since it has been found that this catalyst must be periodically regenerated to remove coke and has a useful life on the order of a few months, it is obvious to those skilled in the art that it would be preferred to have a process which provides for a continuous replacement and regeneration of the catalyst material. Conventionally, processes utilizing the continuous replacement of catalysts utilize as the reaction vessel a fluidized bed wherein the catalyst is fluidized and continuously withdrawn and replaced. However, since the reaction of this invention is endothermic, such a system would require heat addition to the reactor as well as additional heating in the catalyst regeneration step.

Catalytic cracking systems have been described wherein the fluid bed catalyst cracker is replaced by a dilute phase catalytic cracker; see for example *Fluidization and Fluid Particle System*, p. 48 et seq., Zens and Othmer, Reinhold, 1960.

SUMMARY OF THE INVENTION

It has surprisingly been found that oxirane compounds may be prepared in a continuous process by vapor phase deacyloxylation of vicinal hydroxyesters utilizing a dilute phase transport reactor as the reaction zone and a fluidized bed for heating and reactivating the catalyst. The catalyst is heated in a fluidized bed to the temperature necessary for carrying out the deacyloxylation process and transferred to a dilute phase transporter reactor with a co-current stream of reactor feed gas comprising the vicinal hydroxyesters, a carrier gas and inert gas. The product gas exits from the transport reactor and is separated from the catalyst in a cyclone separator. The catalyst is returned to the fluidized bed heater and the product gas treated further to recover product.

DETAILED DESCRIPTION OF THE INVENTION

This invention relates to a continuous process for the preparation of oxirane compounds from a vicinal hydroxyester by vapor phase deacyloxylation of the esters in the presence of a basic material. The overall reaction is described by the equation.

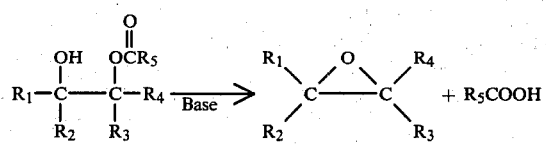

wherein $R_1$, $R_2$, $R_3$, $R_4$, and $R_5$ are as previously described. In the preferred embodiment the vicinal hydroxyester is derived from an olefin compound selected from the group consisting of ethylene, propylene, butylene, pentene, styrene or alpha methyl styrene, and $R_5$ is methyl, ethyl or propyl.

The hydroxyesters may be fed directly to the reaction zone or, if desired, delivered with a carrier gas. The carrier gas acts as a heat sink and also serves to lower the partial pressure of the hydroxyesters in the reaction. The carrier gas may be a liquid, i.e., condensable at room temperatures, such as benzene, toluene, xylene, or pseudocumene. Non-condensable carrier gases may also be used; these include nitrogen, helium, methane and carbon dioxide. Preferably, the carrier gas comprises the corresponding glycols or glycol diesters of the vicinal hydroxyesters used as feed stock; see, for example, U.S. Pat. No. 4,012,424 incorporated herein by reference. Generally, where a carrier is used, the hydroxyesters are about 10 to about 75 percent by weight, preferably about 25 to about 60 percent by weight of the feed.

Reaction conditions must be sufficient to maintain the hydroxyesters in the vapor phase. Suitable temperatures for carrying out the reaction will vary depending on the particular hydroxyester, the concentration of the hydroxyester in the carrier gas and the total system pressure.

Generally deacyloxylation of the hydroxyester proceeds at a temperature of about 250° C. to about 600° C., preferably about 250° to about 500° C., and most preferably about 350° to about 450° C. A wide range of pressures may be used, including high pressures up to 400 psi and vacuum down to 0.1 psia. Of paramount importance is the partial pressure of the hydroxyester in the feed stream. Generally, partial pressures over 100 psi are not used and for ease of operation atmospheric pressure is often preferred. However, surprisingly, it has been found that low pressure operation results in high conversions without loss of selectivity. More specifically, therefore, it is preferred that the partial pressure of the hydroxyester in the feed be about 0.5 to about 15 psia, more preferably about 1 to about 8 psia.

The contact time of the hydroxyester within the reactor is about 0.001 to 20 seconds, preferably about 0.2 to about 5 seconds and most preferably about 0.5 to 2 seconds.

The catalyst of this invention is a basic material used per se or deposited onto or incorporated into a suitable insert support carrier such as alumina, carborundum or silica. The term "catalyst" as used in the specification and claims means both the neat catalyst compound and the catalyst compound on or incorporated into a suitable inert support material.

The basic materials which may be used as catalysts include salts of organic acids and alkali or alkaline earth metals as well as the inorganic salts and oxides of those metals. The preferred catalysts are alkaline silicates and carboxylates. Preferably, the carboxylate is of the same $R_5$ moiety as previously described which makes up the ester group of the vicinal hydroxyester. The preferred catalysts are the silicates and carboxylates of sodium, potassium, lithium, calcium and barium; more preferably, sodium or potassium silicate.

Other compounds which may be used as catalysts are the borates, phosphates, oxides, and carbonates of Group I, II and IIIA metals; see for example U.S. Pat. No. 4,012,423 incorporated herein by reference.

Non-limiting illustrative examples of catalysts of this invention include sodium acetate, potassium acetate, calcium acetate, sodium borate, potassium metaborate, calcium metaborate, sodium aluminate, sodium silicate and potassium silicate.

Surprisingly, it is preferred that the catalyst not have a high surface area. Preferably the surface area of the catalysts should be about 0.15 to about 20 square meters per gram; more preferably about 0.15 to about 10 $M^2/gm$; most preferably about 0.15 to about 2 $M^2/gm$. At higher surface area to weight ratios there is less selectivity toward the formation of the desired products.

As is described in U.S. Pat. No. 4,012,423, incorporated herein by reference, not wishing to be bound by theory, it is believed that the basic material is not truly catalytic in that it takes part in the reaction. For example, where propylene oxide is to be formed from propylene hydroxyacetate using sodium acetate as the basic material, the acetate portion of the basic material first reacts with the hydroxyl group of the hydroxyacetate, thereby activating the remaining oxygen atom. The activated oxygen attaches to the acetate carbon forming the propylene oxide and splitting off a mole of acetate ion. The acetate ion thus generated reacts with the sodium ion from the original sodium acetate and provides additional sodium acetate which in turn reacts with another mole of the feed. Thus it can be seen that the basic material in the reaction zone is in dynamic mobile equilibrium and is continuously regenerated. This dynamic equilibrium enables the process to be carried out with a small amount of the basic material, thus giving the basic material the appearance of functioning catalytically.

It is believed that the basic salts and oxides useful as catalysts are converted in situ to the carboxylate in the manner described above. Notwithstanding the fact that the theory suggests that the basic material is not a catalyst in the classical sense, the term "catalyst" is used in the specification and claims to describe the basic material and its apparent function in the reaction process.

In the process of this invention the reaction is carried out in a dilute phase transport reactor. The reactor feed gas and the fluidized catalyst are fed into the reactor simultaneously at temperatures sufficient to insure that the temperature in the reactor is at the deacyloxylation temperature. Generally, both gases are in the deacyloxylation temperature range. Preferably, the catalyst is at a higher temperature. The reaction takes place as the catalyst is transported through the reactor. The product effluent is separated from catalyst in a cyclone separator, the catalyst being returned to fluid bed catalyst heater. Secondary cyclone treatment is used to further purify the product stream, which is ultimately treated to recover product.

The catalyst is broadly of a particle size of about twenty to two hundred microns. The gas velocity in the transport reactor is about twenty to about seventy feet per second while the volume fraction of catalyst in the cracker is about 0.25 to about 5.0 volume percent.

The term "Dilute Phase Transport Reactor" as used in the specification and claims means the reactor of this invention into which is introduced a catalyst stream and a feed stream while the term "Dilute Phase Transport Reactor System" as used in the specification and claims means the reactor, the fluid bed catalyst heater and the associated equipment used with those units.

Referring now to the figure, the fluid bed catalyst heater, 1, contains a sufficient inventory of catalyst, 13, to permit recycling of catalyst, 13, as herein described. The actual quantity of catalyst, 13, will depend on the size of the dilute phase transport reactor, 2, selected and the volume of the reactor feed gas. Since the elements of a fluid bed are substantially standard, the heater, 1, is shown in schematic. The catalyst, 13, is heated to approximately 420° C. by a source of salt in heater tubes, 11. The inert fluidizing medium, preferably nitrogen, carbon dioxide or methane, is introduced at an inlet, 9, near the bottom of the heater, 1, below the heater distributor plate. This medium serves to fluidize the catalyst in the fluid bed catalyst heater, 1. Additionally, steam, 8, can be introduced with the inert fluidizing gas in an amount of about 20 mole percent based upon the fluidizing gas. Steam serves to activate the catalyst and reduce coking. Alternately, the catalyst can be regenerated by injection of oxygen into the fluid bed heater under conventional decoking conditions or into a diverted stream of catalyst which is reintroduced into the heater.

The catalyst, 13, is transferred through an outlet line, 7, to the reactor. A flow of inert stripping gas is introduced countercurrent to the outward flow of catalyst in order to strip out of the catalyst stream any stream which may be carried along with the catalyst. An inert gas is utilized to transport the catalyst in the pipe leading to reactor, 2. The feed gas is introduced through an inlet line, 14, and intimately mixes with the catalyst, 13. The reaction is carried out as the catalyst is transported through the reactor, 2.

The effluent from the reactor, 2, is fed into a cyclone separator, 3, to separate the product gas stream from the catalyst, which is returned to the heater, 1, after being stripped of product gases in a stripping column, 4. The overhead from the first cyclone is fed through a transfer line, 10, into a second cyclone, 5, in order to further separate any catalyst fines which may be carried over from the first cyclone, 3. In this transfer line, 10, a liquid quench is injected to terminate the reaction. The catalyst collected in the second cyclone, 5, is thereafter transferred to the heater, 1, through the transfer line, 6.

The effluent from the second cyclone, 5, is carried out through a transfer line, 12, to be further processed to recover product. The inert fluidizing gas used in the heater, 1, is recycled after clean-up and compression.

Though the sizing of equipment will of course depend on the amount of reactor feed gas to be processed, Table I sets forth typical sizing and flow rates for a process utilizing as the catalyst potassium silicate of approximately 50 microns in diameter supported on alumina and having a surface area to weight ratio of 1.0 meters square per gram. The feed gas is the hydroxyacetate esters of propylene. Although the figure shows a single reactor used in conjunction with the fluid bed catalyst heater, 1, the design is such that using the equipment size and parameters which are presented in Table I and the Figure, four such reactors would be required with the catalyst heater described. The fluidizing gas is nitrogen. The propylene glycol diacetate serves as the carrier gas.

TABLE I

Fluid Bed Catalyst Heater
Dimensions - Diameter - 20 ft. Height - 40 ft.
Fluidizing Gas Flow - 237,600 Cubic ft. per hr.
Steam Flow - 1,000 lbs/hr.
Catalyst Inventory - 150,000 lbs.
Entrance Pressure - 13.2 psia.
Pressure Drop across Fluidized Bed - ca. 7.6 psia.
Circulating Salt Heater Capacity - 95.1 $\times$ 10$^6$ BTU/Hr.
Reactor Dimensions:
Diameter - 6.36 ft. Height - 48 ft.
Catalyst Flow to the Reactors - 9.6 $\times$ 10$^6$ lbs/hr.
Entrance Pressure - 6.1 psia.
Exit Pressure - 5.6 psia.
Reactor Feed Gas Temperature - 375° C.
Total Reactor Feed Gas - 1.49 $\times$ 10$^6$ lbs/hr.
Reactor Feed Gas Composition - propylene glycol monoacetate 31.3 wt. %; propylene glycol diacetate 68.0 wt. %; propylene glycol 0.7%.
Partial Pressure of Propylene Glycol Monoacetate - 2.3 psia.

It will be obvious to those skilled in the art that the size of equipment and flow rate of feed gas is not a critical limitation of the process. The aforegoing example of Table I is merely by way of illustration.

The propylene oxide product is recovered from the reaction product gases by chilling the gases to about 0° C. and thereafter distilling the condensate. The propylene oxide is the lowest boiling component condensed.

Although the reaction of this invention could be carried out in a conventional fluidized bed reactor, this method has certain disadvantages. There is considerable backmixing and long contact times. Back-mixing causes reverse reactions and reduces the driving force of the reaction with a consequent lower conversion and selectivity. Additionally, if steam is introduced into the fluid bed reactor to reduce coking, the steam results in water in the condensed product stream which causes hydrolysis of the product during separation. A comparison of various prior art catalytic cracking methods with the method of this invention is set forth in Table II below.

TABLE II

| Reactor | Fixed Bed | Conventional Fluidized Bed | Dilute Phase[2] Transport |
|---|---|---|---|
| Catalyst size | ⅛ inch | 30–80 micron | 30–80 micron |
| Gas velocity (ft./sec.) | 0.5 | 0.15 | 50 |
| Empty tube contact time (sec.) | 1.0 | 3.0 | 0.8 |
| PGMA[1] conversion (%) | 35 | 60 | 40 |
| PGMA selectivity to propylene oxide (%) | 83 | 55 | 86 |

[1]PGMA = propylene glycol monoacetate
[2]Calculations based on system kinetics and gas velocity effects It can be seen from Table II that in addition to avoiding problems referred to above with fluidized bed reactors, the selectivity of the instant process is substantially greater than that of the fluidized bed reactor process. Furthermore, the percent conversion is higher than that for a fixed bed reactor. In fixed bed reactors it is difficult to maintain uniform temperatures and therefore selectivity problems result. Additionally, the heat supply requirements of such a system are much greater than in the system of the instant invention. Furthermore, means for catalyst regeneration and replacement require cumbersome valving and other equipment.

What is claimed is:

1. In a process for preparing an oxirane compound by the deacyloxylation of a vicinal hydroxyester using as a catalyst a basic material, the improvement which comprises carrying out the process continuously in a dilute phase transport reactor by:

(a) heating a fluidized bed of catalyst in a heating zone to the temperature necessary for carrying out the deacyloxylation process;

(b) introducing said heated catalyst and a preheated feed gas stream into the reactor, wherein the deacyloxylation of a vicinal hydroxyester component of the feed gas is accomplished, thereby producing an oxirane compound;

(c) separating the reacted gas stream from the catalyst;

(d) returning the catalyst to the heating zone for reheating; and (e) further processing the reacted gas stream to separate out the oxirane product.

2. The process of claim 1 where the catalyst is supported on an inert support material.

3. The process of claim 1 where the catalyst support material comprises alumina, carborundum or silica gel.

4. The process of claim 1 wherein the gas feed stream comprises a vicinal hydroxyester and a carrier gas for said ester.

5. The process of claim 1 wherein the catalyst is fluidized by an inert gas wherein the inert gas is nitrogen, carbon dioxide or methane.

6. The process of claim 1 wherein the total pressure in the reactor is sub-atmospheric.

7. The process of claim 1 wherein the hydroxyester is propylene hydroxyacetate and the catalyst is potassium silicate or sodium silicate.

8. The process of claim 6 wherein the partial pressure of the vicinal hydroxyacetate in the reactor is about 1 psia to about 8 psia.

9. The process of claim 1 wherein the catalyst is potassium silicate or sodium silicata.

10. The process of claim 1 wherein the catalyst surface area is about 0.15 to about 20 square meters per gram.

11. The process of claim 1 wherein the catalyst surface area is about 0.15 to about 2.0 square meters per gram.

12. The process of claim 1 wherein the reactivating gas is steam.

13. The process of claim 1 wherein the reactivating gas is oxygen containing gas.

* * * * *